(12) United States Patent
deKemp

(10) Patent No.: US 12,390,578 B2
(45) Date of Patent: *Aug. 19, 2025

(54) INFUSION PROCEDURE FOR ENHANCING IMAGE QUALITY

(71) Applicant: Ottawa Heart Institute Research Corporation, Ottawa (CA)

(72) Inventor: Robert A. deKemp, Ottawa (CA)

(73) Assignee: Ottawa Heart Institute Research Corporation, Ottawa (CA)

(*) Notice: Subject to any disclaimer, the term of this patent is extended or adjusted under 35 U.S.C. 154(b) by 0 days.

This patent is subject to a terminal disclaimer.

(21) Appl. No.: 18/669,992

(22) Filed: May 21, 2024

(65) Prior Publication Data

US 2024/0299642 A1    Sep. 12, 2024

Related U.S. Application Data

(63) Continuation of application No. 18/302,499, filed on Apr. 18, 2023, now Pat. No. 11,986,622, which is a continuation of application No. 16/660,989, filed on Oct. 23, 2019, now Pat. No. 11,648,343.

(60) Provisional application No. 62/749,352, filed on Oct. 23, 2018.

(51) Int. Cl.
| | |
|---|---|
| A61M 5/00 | (2006.01) |
| A61B 6/00 | (2006.01) |
| A61B 6/03 | (2006.01) |
| A61B 6/50 | (2024.01) |
| A61M 5/14 | (2006.01) |
| A61M 5/168 | (2006.01) |

(52) U.S. Cl.
CPC ............ *A61M 5/007* (2013.01); *A61B 6/037* (2013.01); *A61B 6/481* (2013.01); *A61B 6/503* (2013.01); *A61B 6/5264* (2013.01); *A61M 5/1409* (2013.01); *A61M 5/16813* (2013.01); *A61M 5/16827* (2013.01)

(58) Field of Classification Search
CPC .................................................... A61M 5/007
See application file for complete search history.

*Primary Examiner* — Joseph M Santos Rodriguez
(74) *Attorney, Agent, or Firm* — William D. Hare; McNeely, Hare & War, LLP

(57) ABSTRACT

Disclosed are methods of radioisotope infusion comprising infusing saline comprising a diagnostic dose of a radioisotope, and delivering a pre-measured volume of push saline. The radioisotope may be $^{82}$Rb, $^{15}$O, $^{13}$N, $^{11}$C or $^{18}$F. The radioisotope is infused in the subject for imaging of the heart using Positron Emission Tomography imaging. The methods confer improved image quality with low background noise, higher signal to noise ratio (SNR) and higher contrast to noise ratio (CNR), leading to better diagnosis and thus eliminating the need of repeating the infusion and imaging which in turn reduces exposure of a patient to radiation.

20 Claims, 1 Drawing Sheet

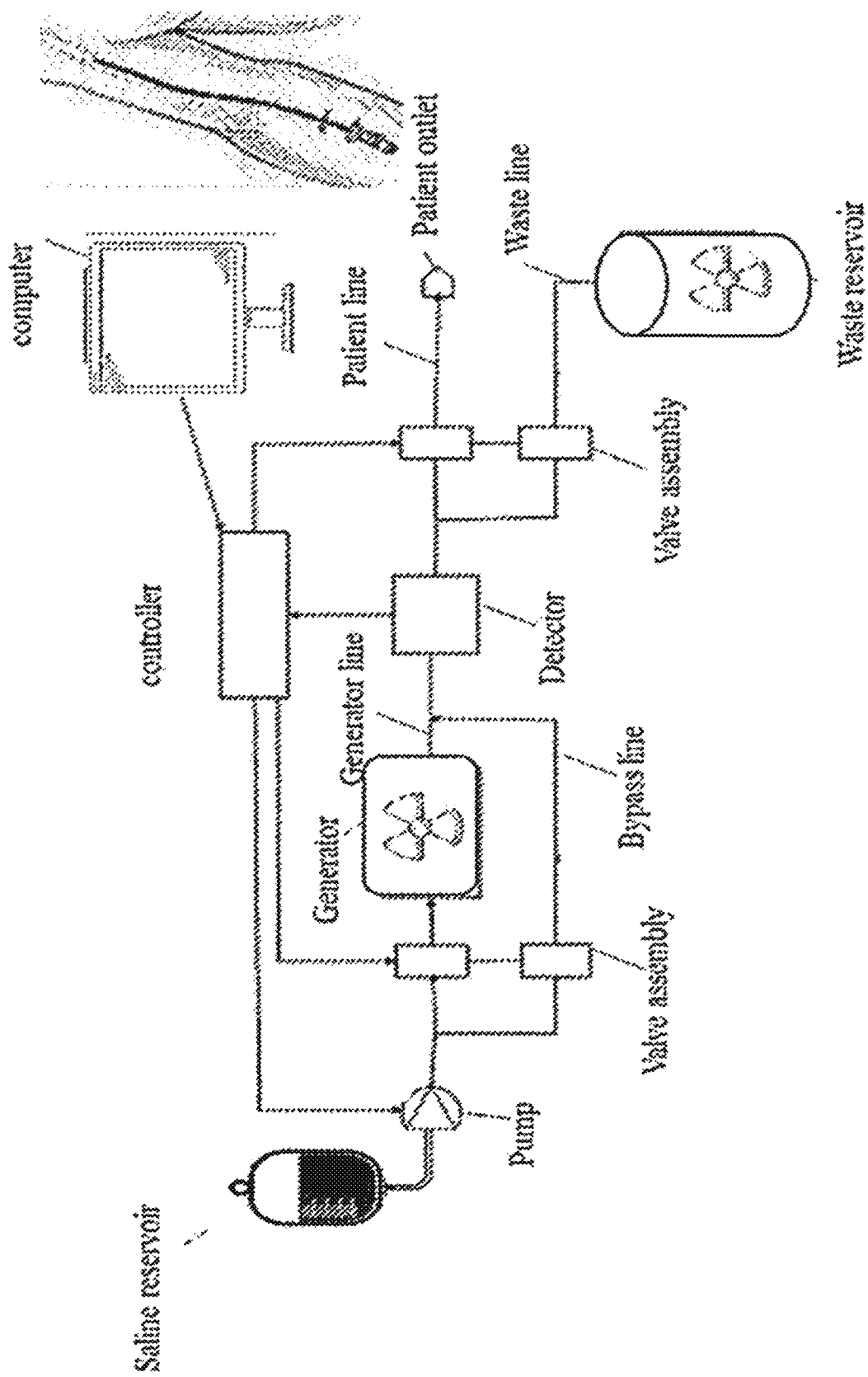

INFUSION PROCEDURE FOR ENHANCING IMAGE QUALITY

TECHNICAL FIELD

The present disclosure relates to radioisotope elution systems and methods for imaging using such systems.

BACKGROUND OF THE INVENTION

Positron Emission Tomography (PET) involves the use of radioisotopes in a non-invasive manner for measurement of relative myocardial perfusion and absolute myocardial blood flow. A limitation of present PET imaging is that infusion of ultra-short half-life tracers over a relatively long period tends to degrade image quality.

U.S. Pub. No. 2015/0228368, assigned to Jubilant Drax-Image Inc. and the Ottawa Heart Institute Research Corporation, discloses a rubidium elution system comprising "patient line flush mode" in which saline flows through the bypass line and come out through patient line. This patient line flush is used prior to elution for expelling air from patient line and after the elution for removal of remaining radioactivity and delivery into patient.

U.S. Pub. No. 2017/0172527, assigned to Bayer HealthCare LLC, discloses a radiopharmaceutical dispensing system comprising intravenous line to inject the radiopharmaceutical into the patient. Saline flush is optionally used to increase 18F-Fludeoxyglucose (FDG) delivered into the patient.

PCT Publication No. WO 2009/152320, assigned to Bracco Diagnostics Inc., discloses a radiopharmaceutical infusion system for rubidium-82 comprising eluant flush at higher flow rate through by-pass line into patient line.

However, these publications, and the prior art generally, have not addressed ongoing problems relating to background noise, signal to noise ratio, contrast to noise ratio, and other issues relating to image quality, that are associated with conventional nuclear medicine imaging procedures that use radioactive materials as contrast agents.

SUMMARY OF THE INVENTION

Accordingly, an object of the presently disclosed methods is to improve image quality with low background noise, higher signal to noise ratio (SNR) and higher contrast to noise ratio (CNR), without increasing the total amount (activity) of radioisotope contrast injection delivered to a patient, which permits better diagnosis and reduces the need for repeating infusion and imaging procedures. This, in turn, reduces exposure of patients to radiation and maximizes image quality.

Disclosed herein are methods for infusing a radioisotope to a subject using a system that includes a controller, an infusion line for delivering fluid under control of the controller, and a pump that is communicatively coupled to the controller, the method comprising infusing a volume of saline containing a diagnostic dose of the radioisotope from the infusion line into a peripheral vein of the subject at a first flow rate that is about 5 mL/min to about 60 mL/min; and, using the controller and pump to deliver a pre-measured volume of push saline in one or more increments to the peripheral vein at a second flow rate that is about 5 mL/min to about 60 mL/min, and the second flow rate is equal to or higher than the first flow rate.

Also provided herein are methods for obtaining a diagnostic image of a subject's heart using a system that includes a controller, an infusion line for delivering fluid under control of the controller, and a pump that is communicatively coupled to the controller, the method comprising infusing a volume of saline containing a diagnostic dose of the radioisotope from the infusion line into a peripheral vein of the subject at a first flow rate that is about 5 mL/min to about 60 mL/min, using the controller and pump to deliver a pre-measured volume of push saline in one or more increments through the infusion line, and to the peripheral vein at a second flow rate that is about 5 mL/min to about 60 mL/min, and the second flow rate is equal to or higher than the first flow rate, and, obtaining a diagnostic image of the subject's heart using the radioisotope as an imaging agent.

Also disclosed are diagnostic images of a subject's heart that is obtained using a system that includes a controller, an infusion line for delivering fluid under control of the controller, and a pump that is communicatively coupled to the controller, wherein the image is obtained by infusing a volume of saline containing a diagnostic dose of the radioisotope from the infusion line into a peripheral vein of the subject at a first flow rate that is about 5 mL/min to about 60 mL/min; using the controller and pump to deliver a pre-measured volume of push saline in one or more increments through the infusion line, and to the peripheral vein at a second flow rate that is about 5 mL/min to about 60 mL/min, and the second flow rate is equal to or higher than the first flow rate; and, obtaining the diagnostic image of the subject's heart using the radioisotope as an imaging agent.

BRIEF DESCRIPTION OF THE DRAWINGS

FIG. 1 illustrates a conventional radioisotope elution system used for imaging.

DETAILED DESCRIPTION

The present disclosure can be more readily understood by reading the following detailed description, including the illustrative embodiments.

As used herein, the term "elution system" refers to a radioisotope infusion system intended for generating a solution containing radioisotope, measuring the radioactivity in the solution, and infusing the solution into a patient for diagnosis.

As used herein, the term "generator" or "radioisotope generator" refers to a hollow column inside a radio shielded container. The column is filled with an ion exchange resin and radioisotope is loaded onto the resin.

As used herein, the term "about" preferably means ±10% of the indicated value.

As used herein, the "merge point" refers to a point in a tubing set where a bypass line and a generator outlet line intersect each other.

As used herein, the term "patient line" refers to a tubing segment that connects the merge point to a patient outlet and is used for infusing the patient with radioactive solution.

As used herein, the term "radioactive saline" refers to the saline solution containing radioactive tracer.

As used herein, the term "controller" refers to a computer or a part thereof programmed to perform certain calculations, execute instructions, and control various activities of an elution system based on user input or automatically.

As used herein, the term "tubing set" refers to a system of conduits that is used for carrying fluid from one point to another. Tubing for use in the tubing set may be formed from any appropriate material, including any disposable material or radiation resistant material. For example, the tubing may be formed from flexible silicon material.

As used herein, the term "pump" refers to the component that is used to induce transportation of elution medium from a source to the inlet of a generator. Generally, a medical grade peristaltic pump or a syringe pump may be used in order to provide control and precise flow rates from a generator to a patient infusion line.

As used herein, the term "valve" refers to a component that is used to alternatively prevent or permit fluid flow into a portion of the system. Exemplary valves include pinch valves, divergence valves, solenoid valves, stop-cock valves, or any combination thereof.

As used herein, the term "activity detector" refers to a component that is used to determine the amount of radio-activity present in eluate from a generator, e.g., prior to the administration of the eluate to the patient.

As used herein, the term "transit time" refers to the time required for radioactive saline to move from an intravenous access site to a target site within the patient.

As used herein, the term "saline push" refers to the method of flushing the activity of radioisotope remaining in the patient line or the patient vein towards the target organ to quickly deliver the radioisotope to the target site. The "push saline" can be used to describe the pre-measured volume of saline that is delivered as a result of the saline push. This results in delivery of higher amount of radioactivity to the target site, which in turn leads to enhancement of image quality, high image counts, increase in myocardial uptake factor and improvement of image quality measures such as image signal-to-noise ratio (SNR), contrast-to-noise ratio (CNR), and coefficient of variance (COV). All these factors contribute to improvement of image quality.

As used herein, the terms image signal-to-noise ratio (SNR), contrast-to-noise ratio (CNR), image count, and coefficient of variance (COV) represent measures of image quality.

As used herein, the term "SNR" refers to signal to noise ratio, which is a measure of image quality. SNR can be defined as a ratio of target signal strength to the noise signal strength.

As used herein, the term "CNR" refers to contrast to noise ratio, which is also measure of image quality. CNR can be defined as a difference of target signal strength minus the background signal strength, divided by the noise signal strength.

As used herein, the term "image counts" refers to number of radioisotope disintegrations acquired per unit time by the PET scanner.

As used herein, the term "COV" refers to coefficient of variance, which is a measure of background noise signal to define image quality. The value of calculated COV is used for calculation of SNR and CNR.

The present disclosure provides methods that result in significantly improved image quality during radio-diagnosis procedures.

Disclosed herein are methods for infusing a radioisotope to a subject using a system that includes a controller, an infusion line for delivering fluid under control of the controller, and a pump that is communicatively coupled to the controller, the method comprising infusing a volume of saline containing a diagnostic dose of the radioisotope from the infusion line into a peripheral vein of the subject at a first flow rate that is about 5 mL/min to about 60 mL/min; and, using the controller and pump to deliver a pre-measured volume of push saline in one or more through the infusion line, and to the peripheral vein at a second flow rate that is about 5 mL/min to about 60 mL/min, and the second flow rate is equal to or higher than the first flow rate.

Also disclosed are methods for obtaining a diagnostic image of a subject's heart using a system that includes a controller, an infusion line for delivering fluid under control of the controller, and a pump that is communicatively coupled to the controller, the method comprising infusing a volume of saline containing a diagnostic dose of the radioisotope from the infusion line into a peripheral vein of the subject at a first flow rate that is about 5 mL/min to about 60 mL/min, using the controller and pump to deliver a pre-measured volume of push saline in one or more increments through the infusion line, and to the peripheral vein at a second flow rate that is about 5 mL/min to about 60 mL/min, and the second flow rate is equal to or higher than the first flow rate, and, obtaining a diagnostic image of the subject's heart using the radioisotope as an imaging agent.

Unless specified otherwise, the following description pertains any of the methods disclosed herein.

The first flow rate (the rate at which a volume of saline containing a diagnostic dose of radioisotope is delivered from the infusion line into a peripheral vein of a subject) may be from about 3 mL/min to about 60 mL/min. For example, the first flow rate may be about 3, 4, 5, 6, 7, 8, 9, 10, 12, 14, 15, 16, 18, 20, 22, 24, 25, 26, 28, 30, 32, 34, 35, 36, 38, 40, 42, 44, 45, 46, 48, 50, 52, 54, 55, 56, 58 or 60 mL/min. In certain embodiments, the first flow rate is about 5 mL/min to about 60 mL/min, about 10 mL/min to about 60 mL/min, about 10 mL/min to about 50 mL/min, about 15 mL/min to about 50 mL/min, about 15 mL/min to about 40 mL/min or about 15 mL/min to about 30 mL/min. If the radioisotope-containing saline is delivered in more than one increment, each increment may be delivered at a discrete flow rate, such that respective increments are delivered at the same or different flow rates. For example, if the radioisotope-containing saline is delivered in two increments, the first and second increments may respectively be delivered at the same flow rate or at a different flow rate.

The second flow rate may be lower than, equal to, or greater than the first flow rate. In certain embodiments, the second flow rate is equal to or higher than the first flow rate. In particular instances, the second flow rate is higher than the first flow rate.

The pre-measured volume of saline that is delivered through the infusion line and to the peripheral vein of the subject may be referred to as "push saline". It may be so termed because it functions to push the radioisotope that has been eluted from the generator and any residual amount of radioisotope within the elution system tubing set to the subject's heart. The volume of saline containing the diagnostic dosage of radioisotope may be about 2 mL to about 40 mL. For example, the volume of saline containing the diagnostic dosage of radioisotope may be about 2, 4, 6, 8, 10, 12, 14, 16, 18, 20, 22, 24, 26, 28, 30, 32, 34, 36, 38, or 40 mL. If the pre-measured volume is not delivered in a single bolus, then it may be delivered in two or more separate increments. Each increment preferably contains an equal fraction of the pre-measured volume. For example, if the push saline is delivered in two increments, then each increment preferably contains 50% of the pre-measured volume, and if the push saline is delivered in three increments, then each increment preferably contains about 33.3% of the premeasured volume, and the like.

The second flow rate (the rate at which at least one increment of the pre-measured volume of push saline is delivered) may be from about 5 mL/min to about 300 mL/min. For example, the second flow rate may be about 5, 6, 8, 10, 12, 14, 15, 16, 18, 20, 22, 24, 25, 26, 28, 30, 32, 34, 35, 36, 38, 40, 42, 44, 45, 46, 48, 50, 52, 54, 55, 56, 58, 60, 62, 64, 65, 66, 68, 70, 75, 80, 85, 90, 95, 100, 110, 120, 130, 140, 150, 160, 180, 200, 220, 240, 250, 260, 280, or 300 mL/min. If the push saline is delivered in more than one increment, each increment may be delivered at a discrete flow rate, such that respective increments are delivered at the same or different flow rates. For example, if the push saline is delivered in two increments, the first and second increments may respectively be delivered at the same flow rate or at a different flow rate.

For example, the second flow rate may be about 5 mL/min to about 50 mL/min, about 5 mL/min to about 40 mL/min, about 5 mL/min to about 30 mL/min, about 5 mL/min to about 20 mL/min, or 5 mL/min to about 10 mL/min higher than the first flow rate. In certain embodiments, the first flow rate is about 5 mL/min to about 60 mL/min, 5 mL/min to about 50 mL/min, 5 mL/min to about 40 mL/min, about 5 mL/min to about 35 mL/min, about 10 mL/min to about 30 mL/min, or about 15 mL/min to about 30 mL/min, and the second flow rate is about 5 mL/min to about 50 mL/min, about 5 mL/min to about 40 mL/min, about 5 mL/min to about 30 mL/min, about 5 mL/min to about 20 mL/min, or 5 mL/min to about 10 mL/min higher than the first flow rate higher than the first flow rate. In some embodiments, the first flow rate is about 5 mL/min to about 55 mL/min, and the second flow rate is 10 mL/min to about 60 mL/min, and the second flow rate is 5 mL/min to about 30 mL/min higher than the first flow rate. In some embodiments, the first flow rate is about 15-50 mL/min, and the second flow rate is about 20-60 mL/min, and the second flow rate is about 5-15 mL/min higher than the first flow rate. In further embodiments, the first flow rate is 5 mL/min and the second flow rate is 10 or 15 mL/min; the first flow rate is 10 mL/min and the second flow rate is 15 or 20 mL/min; the first flow rate is 15 mL/min, and the second flow rate is 20 or 25 mL/min; the first flow rate is 20 mL/min and the second flow rate is 25 or 30 mL/min; the first flow rate is 25 mL/min, and the second flow rate is 30 or 35 mL/min; the first flow rate is 30 mL/min and the second flow rate is 35 or 40 mL/min; the first flow rate is 35 mL/min and the second flow rate is 40 or 45 mL/min; the first flow rate is 40 mL/min and the second flow rate is 45 or 50 mL/min; the first flow rate is 45 mL/min and the second flow rate is 50 or 55 mL/min; or the first flow rate is 50 mL/min and the second flow rate is 55 or 60 mL/min.

In some embodiments, the volume of push saline that is delivered from the bypass line is about 2 mL to about 40 mL, and the second flow rate is from about 10 mL/min to 300 mL/min.

In certain embodiments, the volume of push saline that is delivered from the bypass line is about 2 mL to 40 mL, and the saline is delivered from the bypass line starting immediately after elution of the radioisotope from the generator, and continuing over a period of about 0.4 seconds to 4 min following infusion of the radioactive saline. For example, the delivery of the push saline may continue for about 0.5 seconds, 1 second, 3 seconds, 5 seconds, 10 seconds, 20 seconds, 30 seconds, 45 seconds, 1 minute, 1.5 minutes, 2 minutes, 2.5 minutes, 3 minutes, 3.5 minutes, or 4 minutes following infusion of the radioactive saline.

As noted above, the present methods yield a significant improvement in image quality when used pursuant to a radio-diagnosis procedure. For example, the present methods involving the delivery of the push saline as described herein can result in an improvement by about or at least 5, 10, 15, 20, 25, 30, 35, 40, 45, or 50% in the quality of a diagnostic image of the subject that is obtained following the step of delivering the push saline, as compared to a diagnostic image that is obtained pursuant to a method in which push saline is not delivered.

The methods disclosed herein may result in a higher number of image counts with respect to a diagnostic image of the subject that is obtained following the step of delivering the push saline, as compared to a diagnostic image that is obtained pursuant to a method in which push saline is not delivered. For example, the number of image counts for diagnostic images that are obtained pursuant to the present methods may be improved by a factor of at least 1.5 times compared to the number of image counts for diagnostic images that are obtained pursuant to a method in which push saline is not delivered. Such improvement may be by a factor of about 1.5, 1.6, 1.7, 1.8, 1.9, 2.0, 2.1, 2.2, 2.3, 2.4, 2.5, 2.6, 2.7, 2.8, 2.9, 3.0, or more.

The methods disclosed herein may result in an increase in image signal to noise ratio of at least 20% with respect to a diagnostic image of the subject that is obtained following the step of delivering the push saline, as compared to a diagnostic image that is obtained pursuant to a method in which push saline is not delivered. For example, the image signal to noise ratio with respect to a diagnostic image of the subject that is obtained pursuant to the present methods may increase by about 20, 22, 24, 26, 28, 30, 32, 34, 36, 38, 40, 42, 44, 46, 48, 50, 52, 54, 56, 58, 60, 62, 64, 68, or 70% as compared with an image that is obtained pursuant to a conventional method in which push saline is not delivered following infusion.

The methods disclosed herein may result in an increase in image contrast to noise ratio of at least 20% with respect to a diagnostic image of the subject that is obtained following the step of delivering the push saline, as compared to a diagnostic image that is obtained pursuant to a method in which push saline is not delivered. For example, the image contrast to noise ratio with respect to a diagnostic image of the subject that is obtained pursuant to the present methods may increase by about 20, 22, 24, 26, 28, 30, 32, 34, 36, 38, 40, 42, 44, 46, 48, 50, 52, 54, 56, 58, 60, 62, 64, 68, or 70% as compared with an image that is obtained pursuant to a conventional method in which push saline is not delivered following infusion.

The methods disclosed herein may result in an improvement in image background noise by at least 10% with respect to a diagnostic image of the subject that is obtained following the step of delivering the push saline, as compared to a diagnostic image that is obtained pursuant to a method in which push saline is not delivered. For example, the improvement in image background noise with respect to a diagnostic image of the subject that is obtained pursuant to the present methods may be about 10, 15, 17, 19, 20, 22, 24, 26, 28, 30, 32, 34, 36, 38, 40, 42, 44, 46, 48, 50, 52, 54, 56, 58, 60, 62, 64, 68, or 70% as compared with an image that is obtained pursuant to a conventional method in which push saline is not delivered following infusion. Another way to express "improvement" in background noise by at least 10% is to say that background noise is "reduced" by at least 10%.

The methods disclosed herein may result in an improvement in coefficient of variance by at least 10% with respect to a diagnostic image of the subject that is obtained following the step of delivering the push saline, as compared to a diagnostic image that is obtained pursuant to a method in which push saline is not delivered. For example, the improvement in coefficient of variance with respect to a diagnostic image of the subject that is obtained pursuant to the present methods may be about 10, 15, 17, 19, 20, 22, 24, 26, 28, 30, 32, 34, 36, 38, 40, 42, 44, 46, 48, 50, 52, 54, 56, 58, 60, 62, 64, 68, or 70% as compared with an image that is obtained pursuant to a conventional method in which push saline is not delivered following infusion. Another way to express "improvement" in coefficient of variance by at least 10% is to say that coefficient of variance is "reduced" by at least 10%.

Also provided are diagnostic images that are produced according to any of the methods described herein.

The methods disclosed herein may result in a decrease in venous return transit-time in the subject, as compared to conventional methods in which push saline is not delivered. For example, the venous transit time may decrease by about 5, 10, 15, 20, 25, 30, 35, 40, 45, 50, 55, or 60% relative to the venous transit time that occurs pursuant to a conventional method in which push saline is not delivered following radioisotope elution.

In another aspect, the present methods produce an improvement in image quality by reducing the required dose of radioactive material in comparison to a diagnostic procedure where no saline flush is used.

In accordance with the present methods, the controller may deliver the push saline from a bypass line that can be placed in fluid communication with the infusion line via a valve, to the infusion line. As noted below, any suitable valve may be used for this purpose, and in some embodiments, the valve for placing the bypass line into fluid communication with the infusion line may be a pinch valve.

In certain embodiments, the system further comprises a valve assembly that includes at least one valve for diverting fluid among different components of the system, such as among different tubing segments of the system. The valve assembly may include any type or types of valves that that are suitable for liquid valve systems, such as one or more pinch valves, diverter valves, stop cocks, or any combination thereof. In some embodiments, the constant activity flow is controlled using one or more pinch valves. For example, the opening of the bypass line in order to allow the push saline from the bypass line to the infusion line may be effected by use of one or more pinch valves. Control of the valve assembly, such as the opening and closing of valves, may be via the controller.

The radioisotope that is used in accordance with the present methods has a half-life of from about 10 seconds to 10 hours. The radioisotope may be, for example, 82Rb, 15O 13N, 11C, or 18F, although any suitable PET radiotracer may be used.

The diagnostic dose of the radioisotope within the radioactive saline may be at least 5 mCi.

The pump that is used in the present methods may be a peristaltic pump, a syringe pump, a medical grade pump, or any combination thereof.

The push saline may be delivered using a process that is manual, automated, semi-automated, or any combination thereof.

The system may further include an activity detector that is downstream from the generator for measuring radioactivity within a fluid that is downstream from the generator, e.g., that is eluted from the generator. When the system includes an activity detector, the activity detector may be a beta detector, gamma detector, photomultiplier tube, silicon photomultiplier, positron detector, or may represent any combination thereof.

Also disclosed herein are diagnostic images of a subject's heart that are obtained using a system that includes a controller, an infusion line for delivering fluid under control of the controller, and a pump that is communicatively coupled to the controller, wherein the image is obtained by infusing a volume of saline containing a diagnostic dose of the radioisotope from the infusion line into a peripheral vein of the subject at a first flow rate that is about 5 mL/min to about 60 mL/min; using the controller and pump to deliver a pre-measured volume of push saline in one or more increments through the infusion line, and to the peripheral vein at a second flow rate that is about 5 mL/min to about 60 mL/min, and the second flow rate is equal to or higher than the first flow rate; and, obtaining the diagnostic image of the subject's heart using the radioisotope as an imaging agent. The characteristics of the steps of infusing saline containing a diagnostic dose of the radioisotope and using the controller and pump to deliver the pre-measured volume of push saline may be in accordance with any of the characteristics described above in accordance with the presently disclosed methods.

The step of obtaining the diagnostic image using the radioisotope as an imaging agent may be in accordance with conventional processes. For example, the diagnostic image by be obtained using conventional steps associated with Positron Emission Tomography (PET) or with Single Photon Emission Computed Tomography (SPECT) or with planar Gamma Camera (GC) imaging.

FIG. 1 illustrates a conventional radioisotope elution system used for myocardial perfusion imaging. The elution system comprises a reservoir for elution medium, a pump, and a radioisotope generator. In operation, the pump causes the saline solution to flow from the reservoir and through the generator to elute the radioisotope. The active saline eluted from the generator is then supplied to a patient via a patient line through patient outlet. Although conventional systems may include a bypass line, the bypass line in such systems are used (1) to enable the constant-elution activity mode by feedback control of the saline through the generator, or (2) to flush radioisotope out of the elution system tubing set after the desired dose of radioisotope has been measured by the onboard detector. These uses are distinguishable from the presently disclosed methods, pursuant to which the push saline is delivered from the bypass line immediately after the conventional elution in order to shorten transit time to the patient.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention.

What is claimed:

1. A method for infusing a radioisotope to a subject using a system that includes a controller, an infusion line for delivering fluid under control of the controller, and a pump that is communicatively coupled to the controller, the method comprising:

infusing a volume of saline containing a diagnostic dose of the radioisotope from the infusion line into a peripheral vein of the subject at a first flow rate that is about 5 mL/min to about 60 mL/min; and using the controller and pump to deliver a pre-measured volume of push saline in two or more increments to the peripheral vein, wherein a volume of each increment of the push saline is an equal fraction of the pre-measured volume, each increment of the push saline is delivered at a push saline flow rate that is about 5 mL/min to about 60 mL/min, the push saline flow rate is equal to or higher than the first flow rate and the push saline flow rate of each increment may be the same or different;

wherein the radioisotope is selected from the group consisting of $^{82}$Rb, $^{15}$O, $^{13}$N, $^{11}$C and $^{18}$F.

2. The method of claim 1, wherein the delivery of the push saline results in an improvement in image background noise by at least 10% with respect to a diagnostic image of the subject that is obtained following the step of delivering the push saline, as compared to a diagnostic image that is obtained pursuant to a method in which push saline is not delivered.

3. The method of claim 1, wherein the second flow rate is about 5 ml/min to about 20 mL/min higher than the first flow rate.

4. The method according to claim 1, wherein the volume of the saline containing the diagnostic dose of radioisotope is about 2 mL to about 40 mL.

5. The method according to claim 1, wherein the first flow rate is from about 10 mL/min to about 60 mL/min, and the second flow rate is from about 10 mL/min to about 60 mL/min.

6. The method according to claim 1, wherein the volume of push saline that is delivered from the bypass line is about 2 mL to about 40 mL, and the second flow rate is from about 15 mL/min to 60 mL/min.

7. The method according to claim 1, wherein the radioisotope is $^{82}$Rb.

8. The method of according to claim 1, wherein the radioisotope is infused in the subject for imaging of the heart using Positron Emission Tomography imaging.

9. A method for obtaining a diagnostic image of a subject's heart using a system that includes a controller, an infusion line for delivering fluid under control of the controller, and a pump that is communicatively coupled to the controller, the method comprising:

infusing a volume of saline containing a diagnostic dose of the radioisotope from the infusion line into a peripheral vein of the subject at a first flow rate that is about 5 mL/min to about 60 mL/min;

using the controller and pump to deliver a pre-measured volume of push saline in two or more increments through the infusion line, and to the peripheral vein, wherein a volume of each increment of the push saline is an equal fraction of the pre-measured volume, each increment of the push saline is delivered at a push saline flow rate that is about 5 mL/min to about 60 mL/min, the push saline flow rate is equal to or higher than the first flow rate and the push saline flow rate of each increment may be the same or different; and, obtaining a diagnostic image of the subject's heart using the radioisotope as an imaging agent;

wherein the radioisotope is selected from the group consisting of $^{82}$Rb, $^{15}$O, $^{13}$N, $^{11}$C and $^{18}$F.

10. The method of claim 9, wherein the delivery of the push saline results in an improvement in image background noise by at least 10% with respect to a diagnostic image of the subject that is obtained following the step of delivering the push saline, as compared to a diagnostic image that is obtained pursuant to a method in which push saline is not delivered.

11. The method according to claim 9, wherein the radioisotope is $^{82}$Rb.

12. The method of according to claim 9, wherein the radioisotope is infused in the subject for imaging of the heart using Positron Emission Tomography imaging.

13. The method according to claim 9, wherein the delivery of the push saline results in improvement by a factor of at least 1.5 in the number of image counts obtained, as compared to a diagnostic image that is obtained pursuant to a method in which push saline is not delivered.

14. The method according to claim 9, wherein the controller delivers the push saline from a bypass line that can be placed in fluid communication with the infusion line via a valve, to the infusion line.

15. A method for infusing a radioisotope to a subject using a system that includes a controller, an infusion line for delivering fluid under control of the controller, and a pump that is communicatively coupled to the controller, the method comprising:

infusing a volume of saline containing a diagnostic dose of the radioisotope from the infusion line into a peripheral vein of the subject at a first flow rate that is about 5 mL/min to about 60 mL/min; and using the controller and pump to deliver a pre-measured volume of push saline in one or more increments to the peripheral vein at a second flow rate that is about 5 mL/min to about 60 mL/min, and the second flow rate is equal to or higher than the first flow rate;

wherein the radioisotope is selected from the group consisting of $^{82}$Rb, $^{15}$O, $^{13}$N, $^{11}$C and $^{18}$F.

16. The method according to claim 15, wherein the radioisotope is $^{82}$Rb.

17. The method of claim 15, wherein the second flow rate is about 5 ml/min to about 20 mL/min higher than the first flow rate.

18. The method according to claim 15 wherein the volume of the saline containing the diagnostic dose of radioisotope is about 2 mL to about 40 mL.

19. The method according to claim 15 wherein the volume of push saline that is delivered from the bypass line is about 2 mL to about 40 mL, and the second flow rate is from about 15 mL/min to 60 mL/min.

20. The method of according to claim 15, wherein the radioisotope is infused in the subject for imaging of the heart using Positron Emission Tomography imaging.

* * * * *